United States Patent [19]

Ekwall

[11] Patent Number: 5,424,642
[45] Date of Patent: Jun. 13, 1995

[54] MAGNETIC FIELD DETECTOR WITH A RESILIENTLY MOUNTED ELECTRICAL COIL

[75] Inventor: Christer Ekwall, Spanga, Sweden

[73] Assignee: Siemens Aktiengesellschaft, Munich, Germany

[21] Appl. No.: 124,453

[22] Filed: Sep. 22, 1993

[30] Foreign Application Priority Data

Sep. 29, 1992 [EP] European Pat. Off. ......... 92116649.2

[51] Int. Cl.$^6$ .............................................. G01R 33/02
[52] U.S. Cl. ...................................... 324/256; 324/260
[58] Field of Search ................ 324/244, 256, 257, 260

[56] References Cited

U.S. PATENT DOCUMENTS

| | | | |
|---|---|---|---|
| 2,530,178 | 11/1950 | Rathkamp | 324/256 |
| 4,186,324 | 1/1980 | Hartzell, Jr. | |
| 4,887,032 | 12/1989 | Hetrick | |
| 4,931,732 | 6/1990 | Moon | |
| 5,036,286 | 7/1991 | Holm-Kenney et al. | |

FOREIGN PATENT DOCUMENTS 0359697  3/1990  European Pat. Off.

OTHER PUBLICATIONS

"A Vibrating Cantilever Magnetic-Field Sensor," Hetrick, Sensors and Actuators, vol. 16, No. 3 (Mar., 1989), pp. 197–207.

Primary Examiner—Walter E. Snow
Attorney, Agent, or Firm—Hill, Steadman & Simpson

[57] ABSTRACT

A magnetic field detector, particularly for implantable medical apparatuses, has a coil mounted at the free end of a resilient member fixed at its opposite end portion, and a detecting device for detecting, as a measure of a magnetic field, the movement of the coil in the field when fed with an electric current from a controllable current source. The resilient member is bent to form at least two shanks interconnected at one end. The coil is mounted at the free end of one of the shanks and the resilient member is fixed at the free end portion of the other shank.

12 Claims, 4 Drawing Sheets

MAGNETIC FIELD DETECTOR WITH A RESILIENTLY MOUNTED ELECTRICAL COIL

BACKGROUND OF THE INVENTION

1. Field of the Invention

The present invention is directed to a magnetic field detector, particularly for implantable medical apparatuses, of the type having a coil mounted at the free end of a resilient member, which is fixed at an opposite end, and a detecting device for detecting, as a measure of the magnetic field, the movement of the coil, when fed with an electric current from a controllable current source, within the magnetic field which is to be measured.

2. Description of the Prior Art

U.S. Pat. No. 4,887,032 discloses a sensor for measurement of position, or sensing the passage of an object past a point, which sensor comprises a flexible bar member provided with a piezoelectric element. The bar has a free end of which a coil is supported, and is fixed at its opposite end. If the coil is located in a magnetic field, it will move if a current is passed through the coil and this movement of the coil will cause the piezoelectric bar to flex and a corresponding voltage will be produced by the associated piezoelectric element. This sensor is used for measuring the distance from an object to a reference point, or the rate at which an object passes a reference point to which object a magnet is attached or the object is formed of a material of magnetic permeability and is moving in a permanent magnetic field.

For implanted medical devices, like pacemakers, a magnet is often used for testing purposes. The battery status can, for instance, be detected by the application of a magnet to the implanted device. The exact location of the implanted device can often be difficult to determine and therefore it is also difficult to ascertain the correct location at which the magnet should be placed in relation to, e.g., a reed switch within an implanted pacemaker.

In European Application No. 91114252.9 (assigned to the same assignee, Siemens Aktiengesellschaft, as the present application, but as yet unpublished), a magnetic field detector for use in implantable medical devices is disclosed having a movement-sensitive sensor in the form of a piezoelectric plate, to which a coil is attached. The coil moves when fed with current and when located in a magnetic field, the movement of the coil causing the piezoelectric plate to be deformed, and thus generating a signal representative of the movement.

SUMMARY OF THE INVENTION

It is an object of the present invention to provide a magnetic field detector which is an improvement over known detectors, for determining a magnetic field strength with higher sensitivity than in known devices.

The above object is achieved in accordance with the principles of the present invention in a magnetic field detector wherein an inductive coil is mounted on a resilient member which is bent to form at least two shanks which are interconnected at one end of each shank. The coil is mounted at the free end of one of the shanks, and the resilient member is rigidly fixed at the free end of the other shank. Means are provided for detecting movement of the coil, when fed by a controllable current, in the presence of a magnetic field to be measured. The amount of the movement constitutes a measure of the strength of the magnetic field.

By bending the resilient member supporting the coil to form at least two shanks interconnected at one end, a mechanically more flexible construction is obtained. The improved flexibility results in a lower mechanical resonance frequency for the same dimensions of the device, which is an advantage, and a larger bending of the supporting member is obtained when the coil is tilted. If, e.g., a piezoelectric element is applied to the resilient member over the bend to give an electric signal representative of the bending of the member, this construction gives a higher sensitivity.

According to a further embodiment of the detector of the invention, the resilient member supporting the coil is bent into a U-shape with the coil mounted inside the U-shaped member. Thus in this embodiment the resilient member has two bending knees which still further improves the sensitivity of the detector.

According to another embodiment of the detector of the invention, the detecting device is a light source directing a light beam toward a reflector fixed to the coil, and means for recording the movement of the reflected light beam. If the recording means is situated at a long distance from the reflector of the coil, the coil movement will be translated into large readings at the recording means. Thus a detecting device with a high sensitivity is achieved.

In other embodiments of the detector according to the invention, the detecting device can be formed by means for recording the interference pattern produced by incoming and reflected light to determine the movement of the coil from this pattern, or the detecting device can be a variable capacitance device of the kind used in, e.g., capacitive microphones.

According to another version of this last embodiment, the capacitor is selected in combination with the inductance of the coil such that the resulting electrical resonance frequency agrees with the mechanical resonance frequency of the system carrying the coil. An efficient transfer of energy will then be possible, that is, a maximum efficiency is obtained. This is of particular importance when using the detector according to the invention in, for instance, a pacemaker, in which no circuit is allowed to have a current consumption exceeding 1 $\mu$A.

According to another embodiment of the detector of the invention, the current source supplies an adjustable DC current to the coil in addition to the current pulses. This DC current results in a new operating point and in this way the electrical resonance frequency can be adjusted, In order to provide the coil with a high inductance, in a further embodiment the coil is provided with a ferrite core.

DESCRIPTION OF THE PREFERRED EMBODIMENTS

Figure 1:
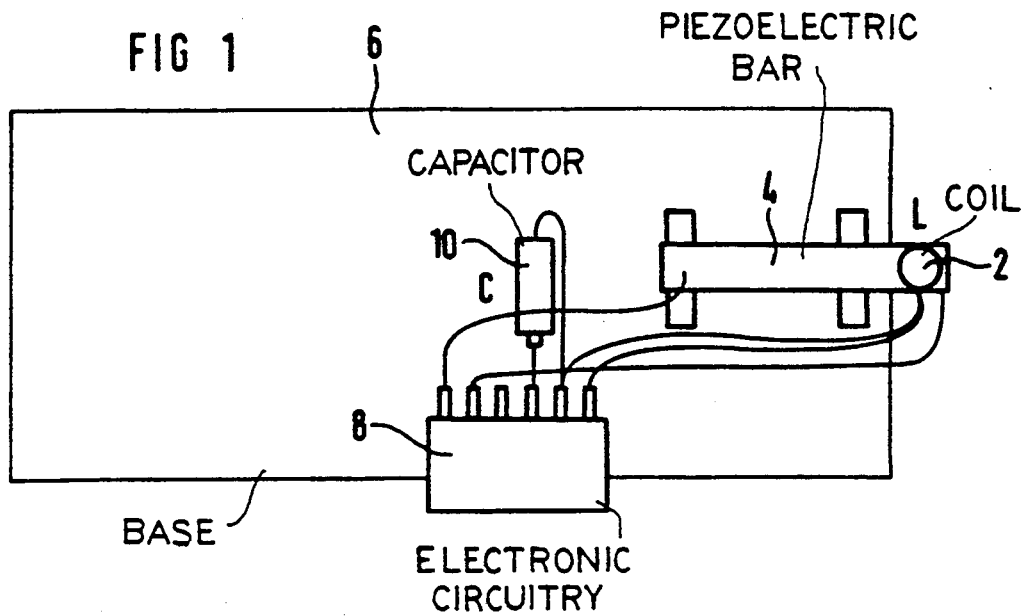
FIG. 1 shows an elevational view and FIG. 2 a side view of a first embodiment of a magnet position detector according to the invention based on the principle of a moving coil.
Figure 2:
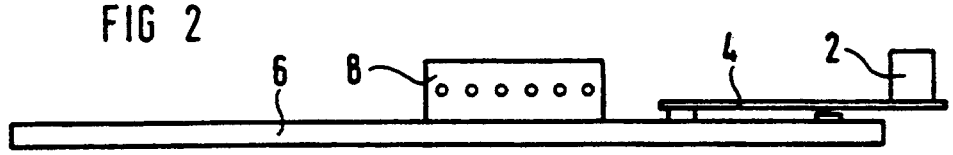
Figure 3:
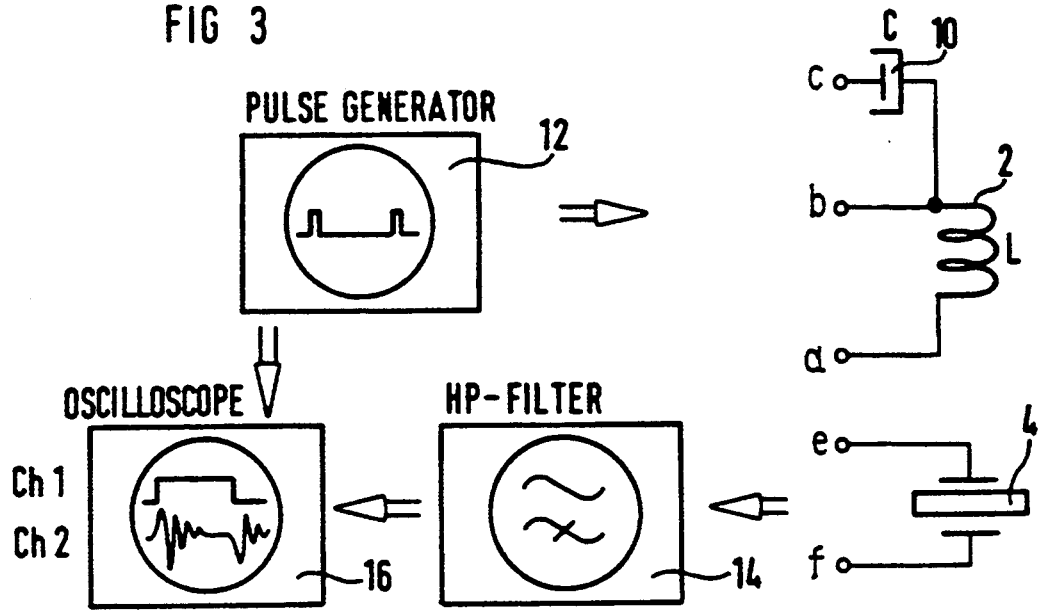
FIG. 3 shows equivalent electrical circuits of the detector together with electric signals used in its operation.

FIGS. 1-3 illustrate the construction and functioning of a magnet position detector according to the invention. The detector is provided with a coil 2 mounted at the free end of a piezoelectric bar 4 which is attached to a base 6 at its opposite end. The electronic circuitry 8 of the detector is also mounted on the base 6. The coil is provided with a core having a non-linear B-H curve, preferably a ferrite core which will also give the coil 2 a high inductance.

The electronic circuitry 8 includes a current source which through the pins a and b of the electronic circuitry 8 is connected to the coil 2. This current source can supply an adjustable DC current to the coil to adjust the operating point of the electrical equipment of the detector. This current source can also be operated as a pulse generator delivering electric pulses directly to the coil 2.

Square pulses are preferably delivered from the electronic circuitry 8 to the coil 2 through a capacitor 10, connected between the pins b and c of the electronic circuitry.

The capacitor 10 is connected in series with the coil 2 and the value of the capacitor 10 is selected such that the electrical resonance frequency of the electrical circuit will be close to the resonance frequency of the oscillating mechanical system. In this way a maximum coupling is obtained with an efficient energy transfer as a result.

Pulses delivered by the electronic circuitry 8 are differentiated by the capacitor 10 and the pulse edges will pass the capacitor and reach the coil 2. If the coil is located in a magnetic field the current passing the coil 2 will excite an oscillation in the piezoelectric bar 4. This oscillation is observed as an electric signal across the piezoelectric bar 4 and supplied to the pins e and f of the electronic circuitry 8 (pin d being unconnected).

Because of the above mentioned resonance, the square pulse will generate a strongly damped electric pulse in the coil 2 with the same polarity as the sides of the square pulse. Thus the oscillations generated by the leading and trailing edges of the square pulse are similar but of opposite directions.

To get a sufficiently high inductance the coil 2 is preferably provided with a ferrite core as mentioned above. Typical figures of the components are inductance L=350 nH, resistance R=1 kohm, capacitance C=150 nF and square pulses are delivered with a frequency of the order of 110 Hz.

FIG. 3 shows the electrical equivalent to the components connected to the electronic circuitry in FIGS. 1 and 2 as well as the signals appearing in the circuit.

The block 12 in FIG. 3 illustrates pulses generated by the pulse generator in the electronic circuitry 8 and fed to the coil 2 through the capacitor 10.

The pulse train is also fed to an oscilloscope 16 which on channel 1 (Ch 1) shows a pulse with an expanded time scale as compared to the pulses shown in square 12.

The pulses supplied to the coil 2 produce an oscillation of the piezoelectric bar 4 in the presence of a magnetic field. The oscillations of the piezoelectric element give rise to a corresponding electric signal delivered to the pins 5 and 6 of the electronic circuitry 8. In the electronic circuitry 8 the signal from the piezoelectric bar 4 is high pass filtered as shown in block 14, and is supplied to channel 2 (Ch 2) of the oscilloscope, square 16. As shown in the oscillogram, a damped oscillation of the piezoelectric bar is produced by the two edges of the pulse, the oscillations at the leading and trailing pulse edges being in opposite phase.

Figure 4:
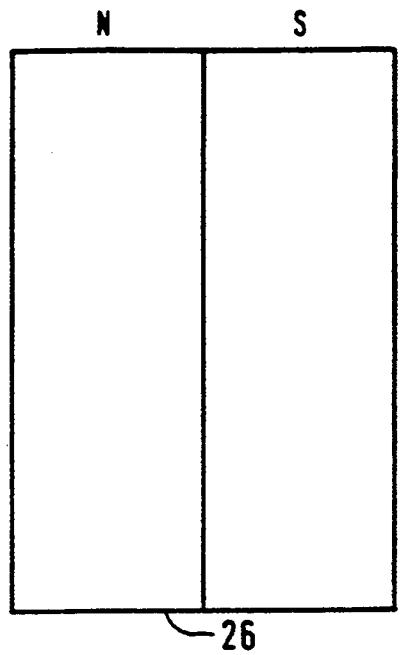
FIGS. 4 and 5 show another coil assembly of the detector according to the invention.
Figure 4:
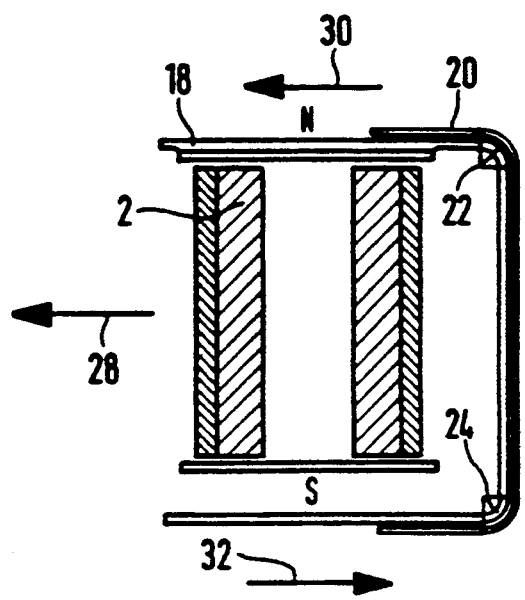
Figure 5:
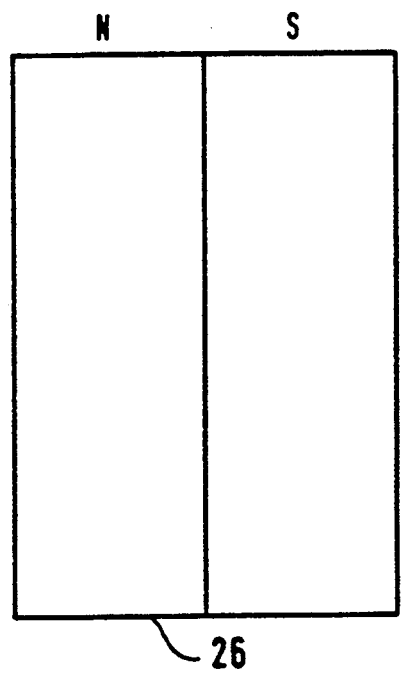
Figure 5:
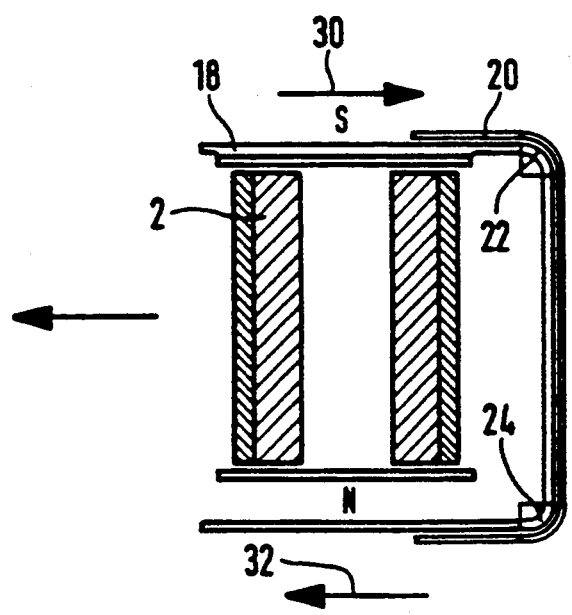

FIGS. 4 and 5 show an advantageous arrangement for mounting the coil 2 on the resilient member. In this embodiment the resilient member is formed of a U-shaped sheet 18, the coil 2 being mounted inside the U-shape at the free end portion of the upper shank in the figures of the U-shaped member. The resilient member is attached to a base or carrier (not shown in FIGS. 4 and 5) at the end portion of the lower shank in FIGS. 4 and 5.

The sheet 18 is formed of a resilient metallic material, such as stainless steel, bronze, titanium, or a plastic material.

On the outer side of the U-shaped member a piezoelectric sheet 20 is fixed over the bends 22 and 24 and the web of the U-member.

The embodiment shown in FIGS. 4 and 5 is more flexible than the construction with a straight bar shown in FIGS. 1 and 2 and results in a lower resonance frequency for essentially the same dimensions of the mechanical system. Further a larger bending, essentially in the bends 22 and 24, is obtained in this embodiment when the coil 2 is tilted. The piezoelectric element 20 delivers a corresponding electric signal to the electronic circuitry 8 and in this way a more sensitive detector is obtained.

To the left in FIGS. 4 and 5 a permanent magnet 26 is shown with its south pole directed towards the coil 2. The coil 2 is centered on the symmetry axis illustrated with the arrow 28. In FIG. 4 the coil 2 is fed with current such that it has a north pole at its upper end and its south pole at the lower end. In FIG. 5 the current, and consequently the poles of the coil 2 are reversed. The arrows 30 and 32 above and below the coil 2 respectively illustrate forces which are acting on the coil because of the magnet 26. As shown, the coil 2 is affected by oppositely directed forces in FIGS. 4 and 5 which will tilt the coil 2 in different directions. Correspondingly different electric signals are then delivered by the piezoelectric element 20. Thus with the detector according to the invention the polarity of the magnet 26 can be determined.

Figure 6:
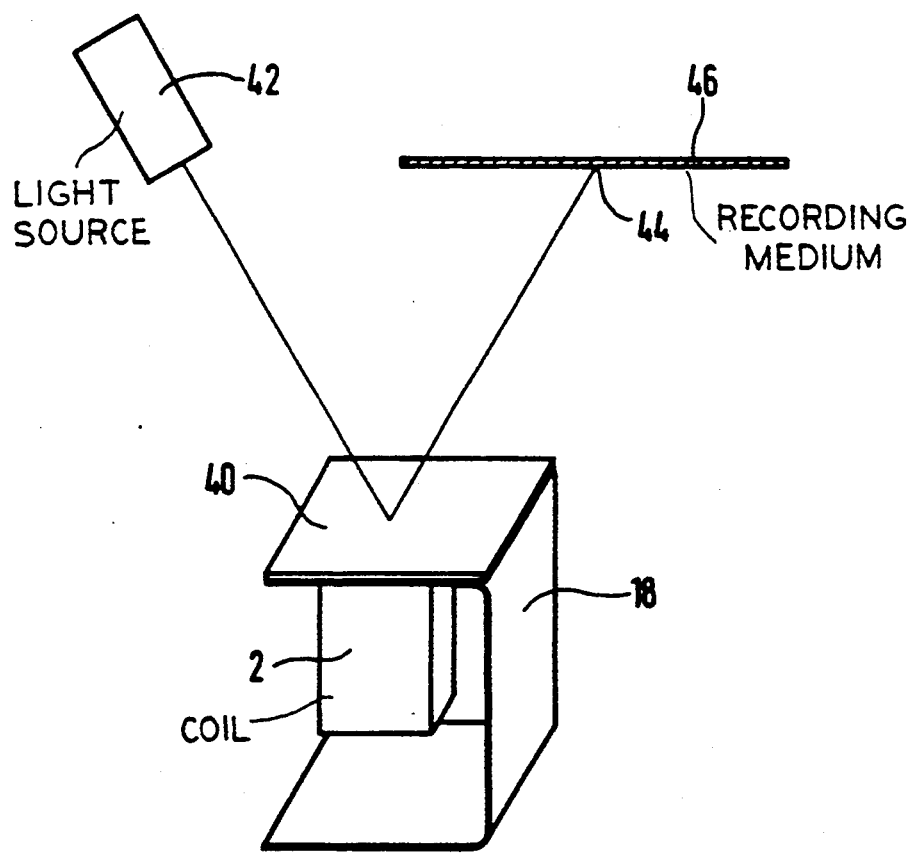
FIGS. 6–8 respectively schematically show three different types of detecting devices for determining the movement of the coil of the detector according to the invention.

FIG. 6 illustrates alternative means for detecting the oscillations of the coil 2. The outer surface 40 of the shank of the flexible member 18 on which the coil 2 is mounted is provided with a reflector, or formed as a reflecting surface. A light source 42, preferably a laser, directs a light beam toward the reflecting surface 40 and the reflected beam is recorded by suitable recording means or recording medium 46. Thus the reflected beam will create a luminous point 44 on the recording medium 46 which point will describe the oscillation of the coil 2 and the shank on which it is mounted.

Figure 7:
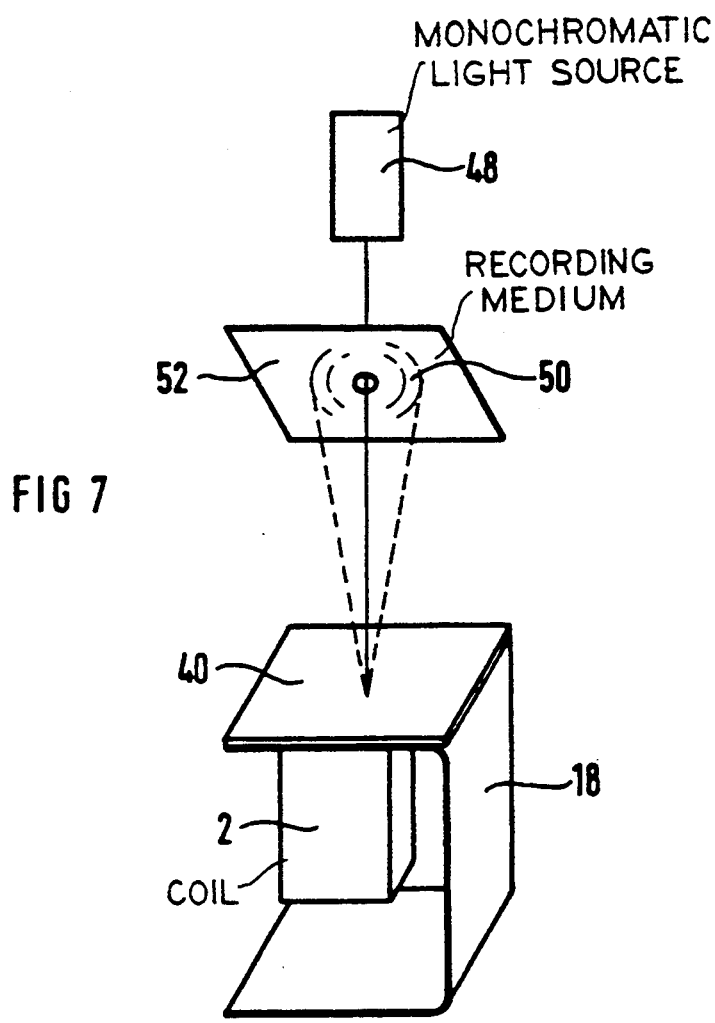

FIG. 7 illustrates an embodiment in which the oscillation of the coil 2 and the flexible member 18 is detected by an interference technique. Also in this case the outer side of the shank on which the coil 2 is mounted is provided with a reflector or a reflecting surface 40. A monochromatic light source 48 directs a light beam toward the reflecting surface 40 and the interference pattern 50 produced by the direct incoming light and the reflected light will reproduce the oscillation of the coil 2 and the flexible member 18. The interference pattern 50 is recorded on a suitable recording medium 52. The appearance of the interference pattern 50 will be determined by the tilting of the coil 2 and consequently be used as a measure of the tilting and thus of the magnetic field strength.

Figure 8:
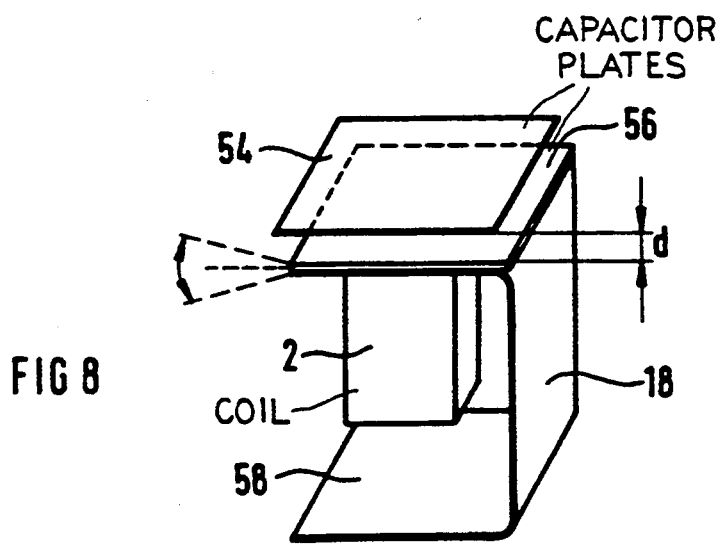

FIG. 8 illustrates a further alternative means for detecting the movement of the coil and the flexible member 18 using a variable capacitance device. The capacitance device has one essentially stationary condenser plate 54 (the fixing of the plate 54 not shown in the figure) and one condenser plate 56 mounted on the shank of the U-shaped member 18 which is carrying the coil 2. Thus when the coil 2 is moving the condenser plate 56 will move together with the coil 2 and the resulting variation in the distance d between the two condenser plates 54 and 56 will result in a capacitance which varies in response to the movement of the coil 2. This capacitance will consequently be a measure of the magnetic field measured by the detector.

Instead of using a separate fixed condenser plate 54 the lower shank of the U-shaped member 18 can form the fixed plate 58 of the variable capacitance device, cf FIG. 8.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic field detector comprising:
   an electrical coil; a resilient member, separate from said coil, on which said coil is mounted, said resilient member being bent to form two shanks which are interconnected by a bend at one end of said resilient member, each shank having a free end, and said coil being mounted at the free end of one of the shanks, and means for rigidly fixing said resilient member at a region of the free end of the other shank for causing said resilient member to vibrate as a whole upon displacement of said coil;
   means for feeding said coil with a controllable electrical current; and
   means for detecting movement of said resilient member caused by displacement of said coil in the presence of a magnetic field, when said coil is fed with said electrical current, as a measure of said magnetic field.

2. A detector as claimed in claim I wherein said means for detecting comprises a piezoelectric element applied to said resilient member covering said bend, and generating an electrical signal representative of deformation of said member caused by movement of said coil in said magnetic field.

3. A detector as claimed in claim 2 wherein said resilient member has a U-shape, and wherein said coil is mounted inside the U-shape of said resilient member.

4. A detector as claimed in claim 2 wherein said resilient member has a U-shape, and wherein said piezoelectric element comprises a sheet of piezoelectric material covering an outer side of said U-shaped resilient member over said bend.

5. A detector as claimed in claim 1 wherein said means for detecting comprises:
   a light source;
   a light reflector fixed to said coil for co-movement therewith for producing a reflected light beam; and
   means for recording movement of said reflected light beam caused by movement of said coil.

6. A detector as claimed in claim I wherein said means for detecting comprises:
   a reflector fixed to said coil for co-movement therewith;
   a monochromatic light source which directs an incoming light beam toward said reflector for producing a reflected light beam; and
   means disposed between said monochromatic light source and said reflector for recording an interference pattern produced by said incoming and reflected light beams, said interference pattern representing movement of said coil.

7. A detector as claimed in claim 1 wherein said means for detecting comprises:
   a variable capacitance having one stationary plate and one plate mechanically coupled to said coil for co-movement therewith; and
   means for detecting variations in the capacitance of said variable capacitance caused by movement of said coil.

8. A detector as claimed in claim 1 wherein said means for feeding said coil with an electrical current comprises means for supplying current pulses to said coil.

9. A detector as claimed in claim 8 wherein said means for supplying current pulses comprises means for supplying square pulses to said coil through a capacitor.

10. A detector as claimed in claim 9 wherein the combination of said coil and said means for resiliently supporting said coil has a natural mechanical resonant frequency, wherein said coil has an inductance, and wherein said capacitor has a capacitance selected for producing an electrical resonant frequency in combination with said inductance of said coil substantially equal to said mechanical resonant frequency.

11. A detector as claimed in claim 8 wherein said means for supplying current pulses further includes means for supplying an adjustable d.c. current to said coil in addition to said current pulses.

12. A detector as claimed in claim 1 wherein said coil has a ferrite core.

* * * * *